United States Patent [19]

Reinhold

[11] 3,976,689

[45] Aug. 24, 1976

[54] PROCESS FOR PREPARING 3-FLUORO-D-ALANINE AND ITS DEUTERO ANALOGS

[75] Inventor: Donald F. Reinhold, North Plainfield, N.J.

[73] Assignee: Merck & Co., Inc., Rahway, N.J.

[22] Filed: Nov. 20, 1974

[21] Appl. No.: 525,708

Related U.S. Application Data

[63] Continuation-in-part of Ser. No. 223,355, Feb. 3, 1972, abandoned.

[52] U.S. Cl. .................. 260/534 C; 260/326.11 R; 260/518 A; 260/534 R
[51] Int. Cl.² ................ C07C 99/00; C07C 101/10
[58] Field of Search ......... 260/534 C, 534 R, 585 C

[56] References Cited
UNITED STATES PATENTS 2,610,212   9/1952   Floyd .............................. 260/534 R
2,839,547   6/1958   Berther ....................... 260/534 C X FOREIGN PATENTS OR APPLICATIONS
38-6884   5/1963   Japan ............................ 260/534 R

OTHER PUBLICATIONS

Adams, Organic Reactions, vol. 7, John Wiley & Sons, Inc., New York (1948) pp. 275 and 276.
Ginsburg, Concerning Amines, Pergamon Press, New York, (1967) pp. 33 to 35.

Primary Examiner—Richard L. Raymond
Attorney, Agent, or Firm—Henry H. Bassford, Jr.; Hesna J. Pfeiffer; Julian S. Levitt

[57] ABSTRACT

3-Fluoro-D-alanine and its deutero analogs, which are potent antibacterial agents, are prepared from fluoropyruvic acid by asymmetric synthesis using an optically active amine such as D-α-methyl-benzylamine.

12 Claims, No Drawings

PROCESS FOR PREPARING 3-FLUORO-D-ALANINE AND ITS DEUTERO ANALOGS

This is a continuation-in-part of application Ser. No. 223,355, filed Feb. 3, 1972, now abandoned.

This invention is concerned generally with the production of 3-fluoro-D-alanine and its deutero analogs, which are potent antibacterial agents valuable in inhibiting the growth of pathogenic bacteria of both the gram-positive and gram-negative types. More particularly, it relates to the preparation of 3-fluoro-D-alanine compounds by asymmetric synthesis wherein fluoropyruvic acid is reacted with a D-optically active amine such as D-α-methylbenzyl-amine to form the corresponding ketimine which is reacted with a reducing agent characterized as adding hydrogen or deuterium to ketimines, such as sodium borohydride, sodium borodeuteride, hydrogen, deuterium, and the like, to form an N-(D-α-methylbenzyl) derivative followed by hydrogenolysis of the methylbenzyl group to form 3-fluoro-D-alanine or 2-deutero-3-fluoro-D-alanine. Alternatively, an amino group of a D-amino acid is enzymatically transferred to the fluoropyruvic acid.

In accordance with the present invention a D-optically active amine compound, such as D-α-methylbenzylamine, R(D)-phenylglycine, 1-amino-(S)-2-[(R)-1-hydroxyethyl]indoline, and the like, are reacted with fluoropyruvic acid, preferably in solution in a lower alkanol such as ethanol, isopropanol, and the like. The reaction is initially conducted in the cold, and is allowed to warm to about room temperature under which conditions the reaction is substantially complete in 1 hour. The resulting D-ketimine such as 2-(D-α-methylbenzylimino)-3-fluoropropionic acid, 2-(D-α-carboxybenzylimino)-3-fluoropropionic acid, and the like, is then reacted with a reducing agent, for example hydrogen under pressure, preferably at about 40 psi in the presence of a hydrogenation catalyst such as palladium-on-carbon catalyst; the hydrogenation is continued until uptake ceases, the catalyst is removed by filtration, and the reduction product is recovered from the filtrate if desired to give N-(D-α-methylbenzyl)-3-fluoro-D-alanine, N-(D-α-carboxybenzyl)-3-fluoro-D-alanine, and the like. Alternatively, the D-ketimine is reacted with an alkali metal borohydride, preferably in isopropanol solution at 10°–25°C., under which conditions the reduction of the D-ketimine is substantially complete in about 3 hours. It is ordinarily preferred to use the resulting solution containing the reduction product directly, or if desired following dilution with water, in the subsequent hydrogenolysis operation.

Similarly, the D-ketimine can be reacted with deuterium under pressure, using the same procedure as specified hereinabove for the reaction with hydrogen; or the D-ketimine may be reacted with an alkali metal borodeuteride using the conditions specified hereinabove for the reaction using alkali metal borohydride; and the solution containing the reduced (deuterated) product can be used as is in the subsequent hydrogenolysis operation or, if desired, the deuterated product can be recovered to give 2-deutero-N-(D-α-methylbenzyl)-3-fluoro-D-alanine, 2-deutero N-(D-α-carboxybenzyl)-3-fluoro-D-alanine, and the like.

A solution of this N-substituted derivative in ethanol or isopropanol, diluted with water if desired, is then reacted with hydrogen at elevated pressure, e.g., 40 psi, using a hydrogenation catalyst such as palladium hydroxide-on-charcoal catalyst, thereby hydrogenolyzing the N-substituent. After hydrogen uptake ceases, the catalyst is filtered, the filtrate is evaporated to dryness in vacuo, and the residual material is recrystallized from aqueous isopropanol to give 3-fluoro-D-alanine or 2-deutero-3-fluoro-D-alanine.

The following examples illustrate methods of carrying out the present invention, but it is to be understood that these examples are given for purposes of illustration and not of limitation.

EXAMPLE 1

A cold solution of 12.1 g. of D-α-methylbenzylamine in 100 ml. of ethanol is slowly added to a solution of 5.3 g. of fluoropyruvic acid in 250 ml. of ethanol, while maintaining the resulting solution at 0°C. The solution is allowed to warm to 25°C. and kept at 25°C. for 1 hour. The solution containing 2-(D-α-methylbenzylimino)-3-fluoro-propionic acid in the form of its salt, is then reacted with hydrogen at 40 psi using 5.0 g. of 10% palladium-on-carbon catalyst, the hydrogenation being continued until uptake ceases; the catalyst is removed by filtration, and the filtrate is evaporated to half-volume. About 100 ml. of water is added to form an aqueous ethanolic solution containing the N-(D-α-methylbenzyl)-3-fluoro-D-alanine, and the methylbenzyl group is hydrogenolyzed at 40 psi using 5.0 g. of 10% palladium hydroxide-on-charcoal catalyst. After hydrogen uptake ceases, the catalyst is removed by filtration, the filtrate is evaporated to dryness in vacuo, and the residual material is recrystallized from 50% isopropanol-water, and then from water, to yield substantially pure 3-fluoro-D-alanine.

EXAMPLE 2

A cold solution of 12.1 g. of D-α-methylbenzylamine in 100 ml. of ethanol is slowly added to a solution of 5.3 g. of fluoropyruvic acid in 250 ml. of ethanol, while maintaining the resulting solution at 0°C. The solution is allowed to warm to 25°C. and kept at 25°C. for 1 hour. The solution containing 2-(D-α-methylbenzylimino)-3-fluoro-propionic acid in the form of its salt, is then reacted with deuterium at 40 psi using 5.0 g. of 10% palladium-on-carbon catalyst, the deuteration being continued until uptake ceases; the catalyst is removed by filtration, and the filtrate is evaporated to half volume. About 100 ml. of water is added to form an aqueous ethanolic solution containing the N-(D-α-methylbenzyl)-2-deutero-3-fluoro-D-alanine, and the methylbenzyl group is hydrogenolyzed utilizing palladium hydroxide-on-charcoal catalyst. After hydrogen uptake ceases, the catalyst is removed by filtration, the filtrate is evaporated to dryness in vacuo, and the residual material is recrystallized from 50% isopropanol-water, and then from water to yield substantially pure 2-deutero-3-fluoro-D-alanine.

EXAMPLE 3

A cold solution of 12.1 g. of D-α-methylbenzylamine in 100 ml. of isopropanol is slowly added to a solution of 5.3 g. of fluoropyruvic acid in 250 ml. of isopropanol, while maintaining the resulting solution at 0°C. The solution is allowed to warm to 25°C. and kept at 25°C. for 1 hour. The solution containing the D-α-methylbenzylamine salt of 2-(D-α-methylbenzylimino)-3-fluoro-propionic acid is then cooled to about 10°C. and 0.66 g. of sodium borodeuteride is added. The reaction mixture is stirred at 25°C. for 3 hours. After 100 ml. of water is added to form an aqueous isopropanolic solution containing the N-(D-α-methylbenzyl)-2-deutero-3-fluoro-D-alanine, and the pH is adjusted to 4.5 with dilute aqueous hydrochloric acid. The methylbenzyl group is then hydrogenolyzed at 40 psi using 5.0 g. of 10% palladium hydroxide-on-charcoal catalyst. After hydrogen uptake ceases, the mixture is heated to 70°C., and the catalyst is removed by filtration. The filtrate is evaporated to dryness in vacuo, and the residual material is recrystallized from 50% isopropanol-water, and then from water, to yield substantially pure 2-deutero-3-fluoro-D-alanine.

EXAMPLE 4

A cold solution of 12.1 g. of D-α-methylbenzylamine in 100 ml. of isopropanol is slowly added to a solution of 5.3 g. of fluoropyruvic acid in 250 ml. of isopropanol, while maintaining the resulting solution at 0°C. The solution is allowed to warm to 25°C. and kept at 25°C. for 1 hour. The solution containing the D-α-methylbenzylamine salt of 3-fluoro-propionic acid is then cooled to about 10°C. and 0.60 g. of borohydride is added. The reaction mixture is then stirred at 25°C. for 3 hours. About 100 ml. of water is added to form an aqueous isopropanolic solution containing the N-(D-α-methylbenzyl)-3-fluoro-D-alanine, and the pH is adjusted to 4.5 with dilute aqueous hydrochloric acid. The methylbenzyl group is hydrogenolyzed at 40 psi using 5.0 g. of 10% palladium hydroxide-on-charcoal catalyst. After hydrogen uptake ceases, the mixture is heated to 70°C., and the catalyst is removed by filtration. The filtrate is evaporated to dryness in vacuo, and the residual material is recrystallized from 50% isopropanol-water, and then from water, to yield substantially pure 3-fluoro-D-alanine.

Instead of using D-α-methylbenzylamine in the reaction with fluoropyruvic acid, other optically active amino compounds may also be employed such as R(D)-phenylglycine or 1-amino-(S-2-[(R)-1-hydroxyethyl] indoline or alternatively, an amino group may be transferred enzymatically, using a D-amino acid oxidase or a D-amino acid specific transaminase, to the fluoropyruvic acid from a D-amino acid such as D-alanine, D-2-aminobutyrate, D-proline, D-phenylalanine, D-methionine, either in their optically pure form, or in admixture with their L-counterpart. For example, 150 μg/ml. of crystalline hog kidney D-amino acid oxidase are added to a solution containing 0.1 M. sodium pyrophosphate buffer, pH 8.5, 40 mM ammonium sulfate, 40 mM sodium 3-fluoro-pyruvate and 8 mM D-proline, and the system is flushed with nitrogen to exclude all oxygen. The mixture is incubated at 25°C. for 4 hours, and the enzyme is inactivated by heating at 95°C. for 2 minutes. The reaction solution is diluted with isopropanol and adjusted to pH 4.8 by addition of aqueous ammonia; the precipitated material is recovered by filtration and dried to give 3-fluoro-D-alanine.

Various changes and modifications may be made in carrying out the present invention without departing from the spirit and scope thereof. Insofar as these changes and modifications are within the purview of the annexed claims, they are to be considered as part of this invention.

What is claimed is:

1. The process which comprises reacting fluoropyruvic acid with an optically active D-amine, thereby forming the corresponding D-ketimine, reacting the latter with a reducing agent characterized as adding hydrogen or deuterium to ketimines, thereby reducing the ketimine to form the corresponding N-substituted 3-fluoro-D-alanine or N-substituted-2-deutero-3-fluoro-D-alanine, and reacting the said N-substituted compound with hydrogen in the presence of palladium hydroxide-on-charcoal hydrogenation catalyst, thereby hydrogenolyzing the N-substituent to form 3-fluoro-D-alanine or 2-deutero-3-fluoro-D-alanine.

2. The process, as defined in claim 1, which comprises reacting fluoropyruvic acid with an optically active D-amine, thereby forming the corresponding D-ketimine, reacting the latter with hydrogen in the presence of palladium-on-carbon hydrogenation catalyst, thereby reducing the ketimine to form the corresponding N-substituted 3-fluoro-D-alanine, and reacting the said N-substituted compound with hydrogen in the presence of palladium hydroxide-on-charcoal hydrogenation catalyst, thereby hydrogenolyzing the N-substituent to form 3-fluoro-D-alanine.

3. The process, as defined in claim 1, which comprises reacting fluoropyruvic acid with an optically active D-amine, thereby forming the corresponding D-ketimine, reacting the latter with deuterium in the presence of palladium-on-carbon hydrogenation catalyst, thereby reducing the ketimine to form the corresponding N-substituted-2-deutero-3-fluoro-D-alanine, and reacting the said N-substituted compound with hydrogen in the presence of palladium hydroxide-on-charcoal hydrogenation catalyst, thereby hydrogenolyzing the N-substituent to form 2-deutero-3-fluoro-D-alanine.

4. The process, as defined in claim 1, which comprises reacting fluoropyruvic acid with an optically active D-amine, thereby forming the corresponding D-ketimine, reacting the latter with an alkali metal borohydride thereby reducing the ketimine to form the corresponding N-substituted 3-fluoro-D-alanine, and reacting the said N-substituted compound with hydrogen in the presence of palladium hydroxide-on-charcoal hydrogenation catalyst, thereby hydrogenolyzing the N-substituent to form 3-fluoro-D-alanine.

5. The process, as defined in claim 1, which comprises reacting fluoropyruvic acid with an optically active D-amine, thereby forming the corresponding D-ketimine, reacting the latter with an alkali metal borodeuteride thereby reducing the ketimine to form the corresponding N-substituted-2-deutero-3-fluoro-D-alanine, and reacting the said N-substituted compound with hydrogen in the presence of palladium hydroxide-on-charcoal hydrogenation catalyst, thereby hydrogenolyzing the N-substituent to form 2-deutero-3-fluoro-D-alanine.

6. The process, as defined in claim 1, wherein fluoropyruvic acid is reacted with D-α-methylbenzylamine to form 2-(D-α-methylbenzylimino)-3-fluoropropionic acid, the latter is reacted with hydrogen in the presence of palladium-on-carbon catalyst thereby forming N-(D-α-methylbenzyl)-3-fluoro-D-alanine, and this N-(D-α-methylbenzyl)-derivative is reacted with hydrogen in the presence of palladium hydroxide-on-charcoal catalyst thereby hydrogenolyzing the methylbenzyl substituent to form 3-fluoro-D-alanine.

7. The process, as defined in claim 1, wherein fluoropyruvic acid is reacted with D-α-methylbenzylamine to form 2-(D-α-methylbenzylimino)-3-fluoropropionic acid, the latter is reacted with sodium borohydride thereby forming N-(D-α-methylbenzyl)-3- fluoro-D-alanine, and this N-(D-α-methylbenzyl)-derivative is reacted with hydrogen in the presence of palladium hydroxide-on-charcoal catalyst thereby hydrogenolyzing the methylbenzyl-substituent to form 3-fluoro-D-alanine.

8. The process, as defined in claim 1, wherein fluoropyruvic acid is reacted with D-α-methylbenzylamine to form 2-(D-α-methylbenzylimino)-3-fluoropropionic acid, the latter is reacted with deuterium in the presence of palladium-on-carbon catalyst thereby forming N-(D-α-methylbenzyl)-2-deutero-3-fluoro-D-alanine, and this N-(D-α-methylbenzyl)-derivative is reacted with hydrogen in the presence of palladium hydroxide-on-charcoal catalyst thereby hydrogenolyzing the methylbenzyl substituent to form 2-deutero-3-fluoro-D-alanine.

9. The process, as defined in claim 1, wherein fluoropyruvic acid is reacted with D-α-methylbenzylamine to form 2-(D-α-methylbenzylimino)-3-fluoropropionic acid, the latter is reacted with sodium borodeuteride thereby forming N-(D-α-methylbenzyl)-2-deutero-3-fluoro-D-alanine, and this N-(D-α-methylbenzyl)-derivative is reacted with hydrogen in the presence of palladium hydroxide-on-charcoal catalyst thereby hydrogenolyzing the methylbenzyl substituent to form 2-deutero-3-fluoro-D-alanine.

10. The process, as defined in claim 1, wherein fluoropyruvic acid is reacted with R(D)-phenylglycine to form 2-(D-α-carboxybenzylimino)-3-fluoro propionic acid, the latter is reacted with hydrogen in the presence of palladium-on-carbon catalyst thereby forming N-(D-α-carboxybenzyl-3-fluoro-D-alanine, and this N-(D-α-carboxybenzyl)-derivative is reacted with hydrogen in the presence of palladium hydroxide-on-charcoal catalyst thereby hydrogenolyzing the carboxybenzyl substituent to form 3-fluoro-D-alanine.

11. The process, as defined in claim 1, wherein fluoropyruvic acid is reacted with R(D)-phenylglycine to form 2-(D-α-carboxybenzylimino)-3-fluoro propionic acid, the latter is reacted with sodium borodeuteride thereby forming N-(D-α-carboxybenzyl)-2-deutero-3-fluoro-D-alanine, and this N-(D-α-carboxybenzyl)-derivative is reacted with hydrogen in the presence of palladium hydroxide-on-charcoal catalyst thereby hydrogenolyzing the carboxybenzyl substituent to form 2-deutero-3-fluoro-D-alanine.

12. The process, as defined in claim 1, wherein the optically active D-amine reacted with fluoropyruvic acid is 1-amino-(S)-2-[(R)-1-hydroxyethyl]indoline.

* * * * *